United States Patent [19]

Green et al.

[11] Patent Number: 4,777,132
[45] Date of Patent: Oct. 11, 1988

[54] ASSAY FOR SALICYLATE

[75] Inventors: Monika J. Green, Leckhamstead; Philip N. B. Gibbs, Oxon, both of Great Britain

[73] Assignee: Medisense, Inc., Cambridge, Mass.

[21] Appl. No.: 847,955

[22] Filed: Apr. 3, 1986

[30] Foreign Application Priority Data

Apr. 3, 1985 [GB] United Kingdom ............... 8508677

[51] Int. Cl.$^4$ ............................................. C12Q 1/26
[52] U.S. Cl. ..................................... 435/25; 435/817; 435/4
[58] Field of Search ................ 435/25, 26, 19, 817, 435/4

[56] References Cited

U.S. PATENT DOCUMENTS 4,416,983  11/1983  Roder ............................... 435/25

FOREIGN PATENT DOCUMENTS 1185155  4/1985  Canada .
0138530  4/1985  European Pat. Off. .

OTHER PUBLICATIONS

Power (1982) Anal. Chem. 54:1985–1987 (1985).
You, Clin. Chim. Acta. 149:283–285 (1985).
Rahni et al., Anal. Chim. Acta. 181:219–225 (1986).
You et al., Clin. Chem. 30(9):1549–1551 (1984).
Longenecker et al., Clin. Chem. 30(8):1369–1371 (1984).
Doskocil: Collection of Czechoslovak Chemical Communications 15, pp. 780–796, (1950).
Proudfoot Australian J. Chem. 36, pp. 885–894 (1983).
Fonong Analytica Chimica Acta 158, pp. 357–362 (1984).

Primary Examiner—Robert J. Warden
Assistant Examiner—Robert Benson

[57] ABSTRACT

The specification discloses a method and apparatus for the assay of salicylate (or a derivative thereof) comprising a conducting body having at a surface thereof an enzyme capable of catalyzing the conversion of salicylate (or a derivative thereof) to a catechol whereby said catechol is subject to direct electrochemical measurement as it oxidizes at said surface to generate a current as a measure of the reaction taking place and thereby of the concentration of salicylate at said surface. The method typically comprises the steps of;

(a) treating a liquid sample suspected of containing salicylate or a derivative thereof with an enzyme capable of catalyzing the conversion of salicylate or a derivative thereof into a catechol, and, (b) measuring the concentration of catechol in the treated sample by direct electrochemistry.

7 Claims, 4 Drawing Sheets

ASSAY FOR SALICYLATE

The present invention is concerned with an assay for salicylate and with apparatus for performing the said assay.

Aspirin (acetyl salicylate) is a popularly used medication. The drug is readily absorbed from the gastrointestinal tract into the portal circulation and is rapidly hydrolysed by hepatic enzymes, largely during its first pass through the liver, to yield free salicylate.

The normal half-life of aspirin in the blood is approximately 25 mins (J.N. Buskin et al., Clin. Chem. (1982). 28 1200) and it has been further found that most of the absorbed aspirin reaches the systemic circulation as free salicylate. This salicylate anion is believed responsible for the analgesic, antipyretic and anti-inflammatory properties of the ingested aspirin (G. Levy, Brit. J. Clin. Pharmacol., (1980), 10, 2855).

The use of aspirin as a short term analgesic/antipyretic agent produces relatively low levels of salicylate in the serum (30–100 mg/l; 0.22–0.73 mM) and consequently monitoring of such levels is not normally necessary. However, the use of aspirin in long term anti-inflammatory doses, such as in the treatment of arthritis, produces much higher salicylate concentrations and it is, therefore, desirable to regularly monitor these levels especially within the therapeutic range of 20 to 300 mg/l; 0.15–2.19 mM; (A. K. Done, Pediatrics, (1970), 26, 800).

The monitoring of salicylate levels is also required in cases of acute poisoning (either accidental or intentional) where the serum concentration can exceed 600 mg/l (4.38 mM). In the case of acute poisoning prognosis and therapeutic intervention are generally dependent on the salicylate ion concentration.

These clinical requirements have led to the development of a variety of methods for monitoring serum salicylate levels such as are briefly described below:

(a) Reaction with Folin-Ciocalteau Reagent

This assay is based on the reaction of phenols with the Folin-Ciocalteau reagent in strong alkali solution to produce a blue colour which can be measured spectrophotometrically/colorimetrically (M. J. H. Smith & J. M. Talbot, Brit. J. Exp. Path., (1950), 31, 65). This method however requires the initial removal of protein from the serum samples and is not very specific for salicylate resulting in high "blank" values.

(b) Reaction with Ferric Salts

A variety of methods are based on the formation of a purple coloured complex when salicylate ions react with ferric salts in dilute acid (P. Trinder, Biochem. J., (1954), 57, 301; Lancer Salicylate Rapid Stat Diagnostic Kit, U.S. Pat. No. 3,915,643; J. H. Eckfeldt & K. M. Nelson, Clin, Chem., (1983), 29, 839).

These procedures require an initial sample workup procedure in order to precipitate protein and other material. High "blank" values occur for controls containing no salicylate due to interference from a variety of compounds, normally present in the body (.E. S. Kang et al., Clin, Chem., (1983), 29, 1012).

(c) Direct Spectrophotometric/Fluorophotometric Methods

Known methods for estimation of salicylate also include a first ultraviolet spectrophotometric method (L. Williams et al., J. Lab. Clin. Med., (1959), 53, 156), and a fluorophotometric method (A. Saltzman, J. Biol. Chem., (1948), 174, 399) A major disadvantage of such procedures is the need for expensive and bulky laboratory equipment.

(d) Liquid-Chromatographic Methods

The quantification of plasma salicylate levels has been achieved using gas liquid-chromatography (L. J. Walter et al., J. Pharm. Sci., (1974), 63, 1754) and high performance liquid-chromatography (J. N. Buskin et al., Clin. Chem., (182), 28, 1200) with far more specificity and sensitivity than the aforementioned methods. However, these liquid-chromatographic procedures require highly skilled laboratory technicians as well a large investment in laboratory equipment.

(e) Enzymic Procedures

More recently, methods have been developed for the measurement of salicylate levels which offer the specificity of an enzymic procedure and do not require any initial sample workup (R. W. Longenecker et al., Clin. Chem., (1984), 30, K.-S. & You and J. A. Bittikoker, Clin, Chem., (1984), 30, 1549). Generally, such methods are indirectly photometric and measure the decrease in absorbance at 340 nm due to oxidation of one of the substrates for the assay enzyme, namely NADH, and consequently still require skilled technical staff and the purchase of expensive laboratory equipment.

One method, however, suggested in Canadian Pat. No. 1 185 155, envisages measurement of the progress of the enzyme reaction by measurement of the oxygen consumed by the reaction. This method, while an electrochemical method, suffers by being subtractive from the initial oxygen content, which can vary, and which must first be ascertained to ensure that usable readings are obtained.

It moreover requires sample dilution, because of the limited oxygen tension within the buffer solution, and hence still requires skilled manipulation. Moreover, a system sealed against inward diffusion from atmospheric oxygen must be used.

Also, since this earlier proposal measures the oxygen product, it can be sensitive to other oxygen-utilising species in the assay system.

It is one aim of the present invention to provide a rapid electrochemical method for the quantification of salicylate in whole blood which in contrast to the above method can be performed by relatively unskilled persons and without the need for bulky and expensive laboratory equipment.

According to the present invention there is provided a method for the assay of salicylate or a derivative thereof which comprises the steps of:
 (a) treating a liquid sample to be assayed for the salicylate or a derivative thereof with an enzyme capable of catalysing the conversion of salicylate or derivative thereof into a catechol, and,
 (b) measuring the concentration of the catechol in the treated sample by direct electrochemistry of the catechol.

Conveniently the liquid sample is contacted with an electrode at a suitable potential which contacts the liquid sample for direct electrochemical measurement of the catechol. a The hydroxylation and simultaneous decarboxylation of salicylate to yield catechol may be catalysed by any suitable enzyme of the type defined as Ec 1.14.13.1 and named as salicylate hydroxylase (otherwise known as salicylate 1-monooxygenase) by the International Union of Biochemistry (Enzyme Nomenclature, 1978, Academic Press, New York, (1979).

The enzyme is usually a salicylate hydroxylase isolated from a bacterium, which is preferably a species of Pseudomonas, most especially Pseudomonas sp RPP (ATCC 29351) or Pseudomonas sp RWS (ATCC 29352).

Such an enzyme material is preferably purified by ion-exchange chromatography, e.g. on an ion-exchange anion column. Fast protein ion exchange chromatography on a Polyanion SI column (Pharmacia) is of particular value.

Any dissolved salicylate sample is susceptible of treatment in accordance with the invention.

Conveniently, however, the sample comprises whole blood. It may, possibly, comprise plasma, serum, or any other like body fluid.

In carrying out the method the liquid sample may conveniently be contacted with an electrode having at its surface a layer comprising at least the said enzyme, usually in admixture with NADPH.

In one mode of use, a blood sample is applied onto the sensor. If the blood sample contains salicylate and the second substrate of the hydroxylase enzyme (NADH) is available for the enzyme (i.e. in the sample or on the electrode catalytic current is generated by the product (catechol) at the electrode surface. The potential is poised to oxidise the catechol and the current is measured.

Such electrodes themselves, especially when configured as a throw-away strip, and analytic equipment for salicylate, usable for whole blood samples, having such an electrode located or locatable therein also constitute aspects of the present invention.

In order that the invention may be better explained, it will be described by way of example and with reference to the accompanying drawings wherein.

Figure 1:
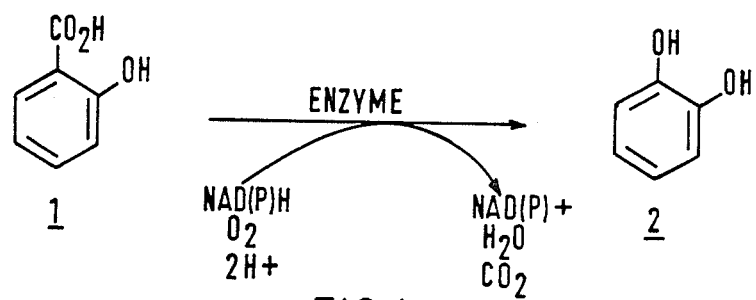
FIG. 1 is a postulated reaction scheme for the enzymic reaction.

As shown in FIG. 1, the enzymic conversion of salicylate (1) to catechol (2) appears to be unidirectional and to occur in the presence of NAD(P)H and molecular oxygen.

Figure 2:
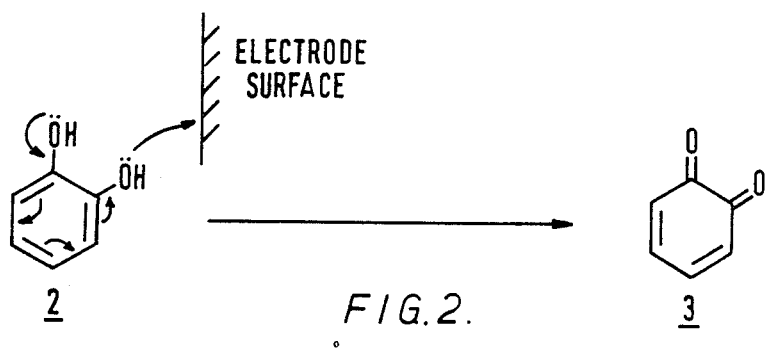
FIG. 2 is a postulated reaction scheme for the reaction at the electrode surface.

As shown in FIG. 2, in this scheme catechol (2) is converted into the orthoquinone (3) at the electrode surface and at a suitable oxidising potential.

The removal of electrons from the catechol (2) results in the formation of ortho-quinone (3) or a derivative thereof, and may be employed both as a qualitative indicator of the presence of the catechol and hence the salicylate, and as a quantitative assay for the catechol and hence as an indirect measure of the concentration of salicylate at the electrode surface.

EXAMPLE 1

Cyclic Voltammetry of Catechol

A buffer solution was prepared from potassium dihydrogen phosphate (1.77g; Analar from British Drug House (BDH) and di-potassium hydrogen phosphate (19.6 g; Analar from BDH), which were dissolved in distilled water, adjusted to pH 7.6 and made up to a final volume of 1 liter. Catechol (from Sigma Chemical Company) was dissolved in such a buffer solution and degassed under reduced pressure immediately prior to use.

The electrodes were made of a range of different materials, especially gold and glassy carbon, most especially pyrolytic graphite. The electrodes were polished between runs using a slurry of 0.3 $\mu$m alumina (BDH) made up with water. The object of this polishing was to remove impurities and oxidation products from the surface of the electrode. The alumina was removed from the electrode surface by ultrasonication.

Cyclic voltammograms were produced from a range of solutions by sweeping the potential difference from zero to +500 mV and back down to −100 mV vs. S.C.E. The potential applied was controlled by a potentiostat (from Jaytron Inst. A.S. Scientific. Abingdon) using a scan rate of 50 mv/s.

Figure 3:
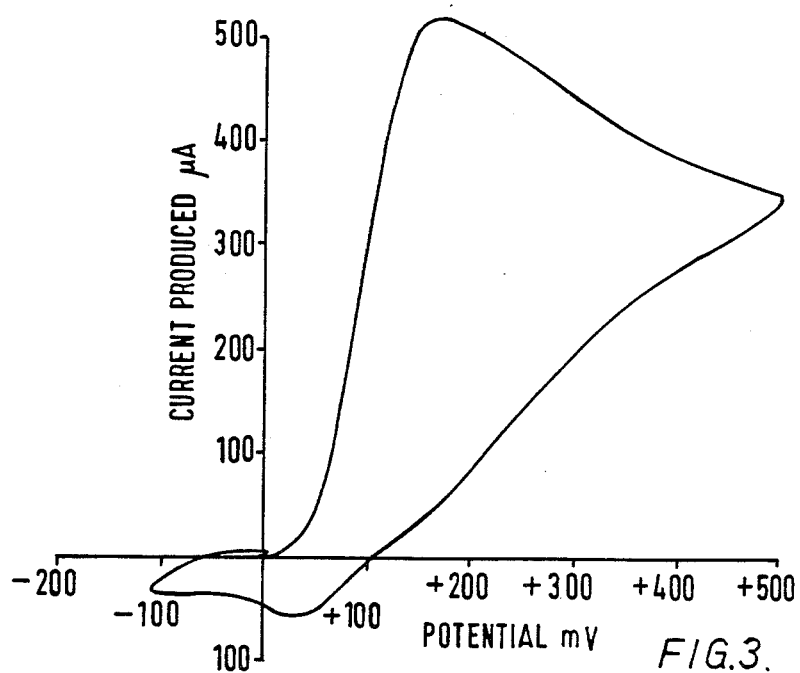
FIG. 3 shows a cyclic voltammogram of catechol at 10 mM final concentration.

The oxidation current produced was recorded on a Gould Series 60000 Chart Recorder in which the X-axis recorded the applied potential and the Y-axis recorded the current produced. A cyclic voltammogram of catechol (at 10 mM final concentration) is shown in FIG. 3.

EXAMPLE 2

Sensor Incorporating Salicylate Hydroxylase

Salicylate sodium salt (GOLD LABEL and available in the marketplace from Aldrich) was dissolved in the phosphate buffer to give a final concentration of 0.1M.

NADH disodium salt (Grade II; from Boehringer Mannheim) was dissolved in buffer solution to give a final concentration of 0.2M.

Salicylate hydroxylase (from the Signal Chemical Company) was resuspended in distilled water to give a stock solution of 20 units/ml (based on the manufacturers information and unit definition).

The electrodes used were identical to those described above with reference to Example 1.

The solution of salicylate hydroxylase (from Sigma Chemical Company) was routinely assayed at 37° C. by following the decrease in absorbance at 340 nm (due to the oxidation of one of the substrates, NADH).

To a 1 ml glass cuvette was added 10 $\mu$l of salicylate solution, 10 $\mu$l of NADH (0.02M solution) and 977.5 $\mu$l of phosphate buffer solution. The cuvette was placed in a Pye Unicam SP8-400 spectrophotometer which had been thermostatted at 37° C. After the addition of salicylate hydroxylase solution, the decrease in absorbance was followed at 340 nm. It is known that one unit of enzyme will convert one $\mu$mole of salicylate and NADH to catechol and NAD+ per minute at pH 7.6 and at a working temperature of 37° C.

In the cyclic voltammograms the cell contained 52 $\mu$l of NADH solution (0.2M, as above), 60 $\mu$l of salicylate hydroxylase solution and 428 $\mu$l of buffer solution.

Cyclic voltammograms were recorded both in the absence and in the presence of the substrate (60 μl salicylate). In order to ensure that the reaction progressed, each sample was incubated at 37° C. for 2 minutes prior to initiating the scan.

Figure 5:
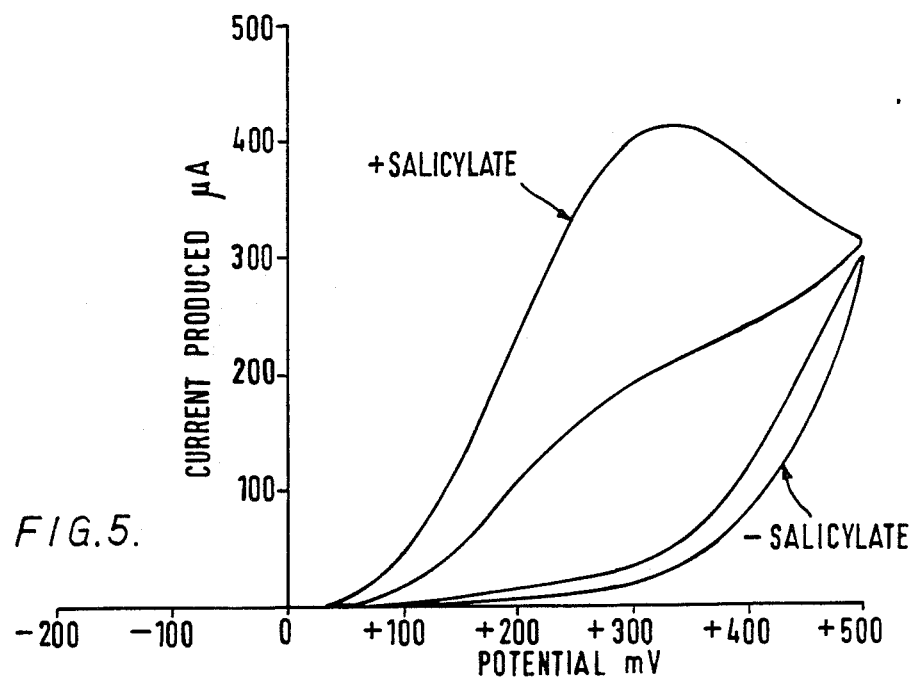
FIG. 5 shows a cyclic voltammogram of NADH solution, salicylate hydroxylase solution and buffer solution, both in the absence and in the presence of salicylate.

Such a cyclic voltammogram is shown in FIG. 5, and it will be noted that the addition of the salicylate substrate to the incubation mixture prior to initiation of the scan, results in a marked change in the profile of the curve obtained.

EXAMPLE 3

Steady state measurements

In steady state measurements the current produced upon application of a fixed potential to a stirred solution was measured on the Y-axis of the chart recorder using the X-axis as a time base. The potential was poised at +250 mV vs SCE at 37° C. after allowing 2 minutes for the system to come to equilibrium. Stirring of the solutions ensures that the layer of material close to the electrode and which is available for oxidation is replenished and thus the current produced at the electrode does not decay due to exhaustion of reagents.

Figure 4:
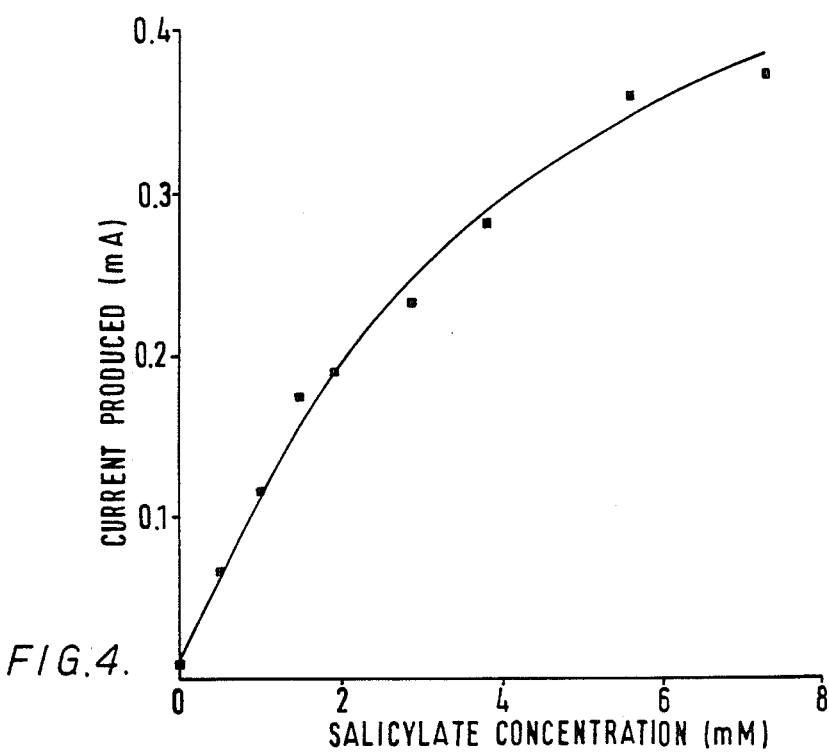
FIG. 4 shows a calibration curve for salicylate obtained by a series of steady state electrochemical measurements in the presence of increasing amounts of salicylate solution.

The stirred solutions comprised; 140 μl of NADH solution, 100 μl of salicylate hydroxylase solution and 760 μl of buffer solution. Steady state electrochemical measurements were made in the presence of increasing amounts of salicylate solution to produce a calibration curve for salicylate and is shown in FIG. 4. The current measured was obtained by poising the electrode at +250 mV vs S.C.E. 2 minutes after addition of the sample. This calibration curve can be used in conjuction with direct readings of unknown samples in order to determine the salicylate ion.

EXAMPLE 4

Purification of salicylate hydroxylase

A buffer solution was prepared from Trisma base (2.42g;Signal Chemical Company) dissolved in distilled water, adjusted to pH 7.5 and made up to a final volume of 1 liter. This buffer solution (buffer A) is used to apply the enzyme sample to the ion exchange column. A second buffer solution was prepared (buffer B). Buffer B was essentially the same as buffer A but also contains 150 mM sodium sulphate (BDH). This buffer is used to elute the enzyme from the anionic column.

Salicylate hydroxylase (from GDS Technology Inc.) was resuspended in buffer solution A to give a stock solution of 50 units/ml (18 mg protein/ml) based on the manufacturers information and definition of activity and units.

Protein purification was performed on a complete Pharmacia FPLC (Trade Mark) system. A Pharmacia Polyanion SI column (HR5/5) was equilibrated with buffer A. The enzyme solution (16Oul) was applied to the column at a flow rate of lml min$^{-1}$. The sample was eluted from the column using a preprogrammed gradient (see FIG. 6).

Figure 6:
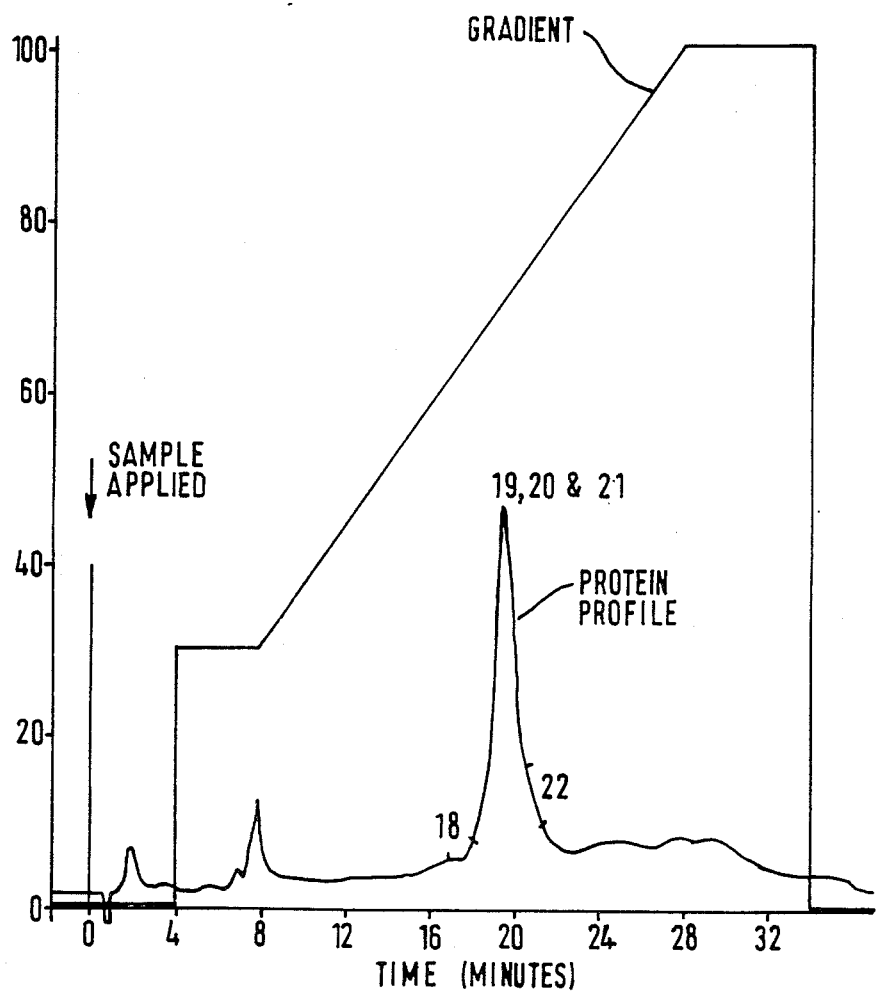
FIG. 6 shows the separation profile of Pseudomonad proteins by FPLC using ion exhange chromatography to obtain pure salicylate hydroxylase.

Fractions (lml) were collected in the FRAC-100 fraction collector (Pharmacia) and were assayed for enzyme activity as detailed in Example 2. Enzyme activity was present in fractions 20 and 21 and was associated with a protein peak. The profile of the chromatographic separation is shown in FIG. 6.

The specific activity of the enzyme was in excess of 10 units/mg usually 14 to 15 units/mg.

The purification of salycylate hydroxylase has been scaled up using polyanion SI-17um packed into large column (1.6cm×45cm). Similar activities have been reported in the literature using several purification steps. (You, K-S & Roe, C. R. Anal Biochem (1981,114, 177; Kamin, H. et al, Methods in Enzymology (1978),53,527). We belive this method has many advantages over existing purification protocols.

EXAMPLE 5

Dry Strip Sensor for Salicylate

Sodium salicylate and NADH were obtained from the same sources as detailed in Example 2 and dissolved in 0.9% saline to give final concentrations of 20 mM. These two solutions were mixed in various proportions to give a range of salicylate concentrations in 10mM NADH.

BES (NN'-Bis(2-hydroxyethyl-2-aminoethane sulphonic acids; 32.0 g from BDH), sodium azide (0.5 g;from BDH) and FAD disodium salt (85mg; from BDG) were dissolved in distilled water. adjusted to pH7 and made up to a final volume of 1 liter.

The purified salicylate hydroxylase was ultraconcentrated using an Amicon ultrafiltration cell containing a 10,000 molecular weight cut-off filter and the buffer was concentrated to 520 units/ml.

Dry strip electrodes were prepared according to British Patent Application No. 8515884.

Figure 7:
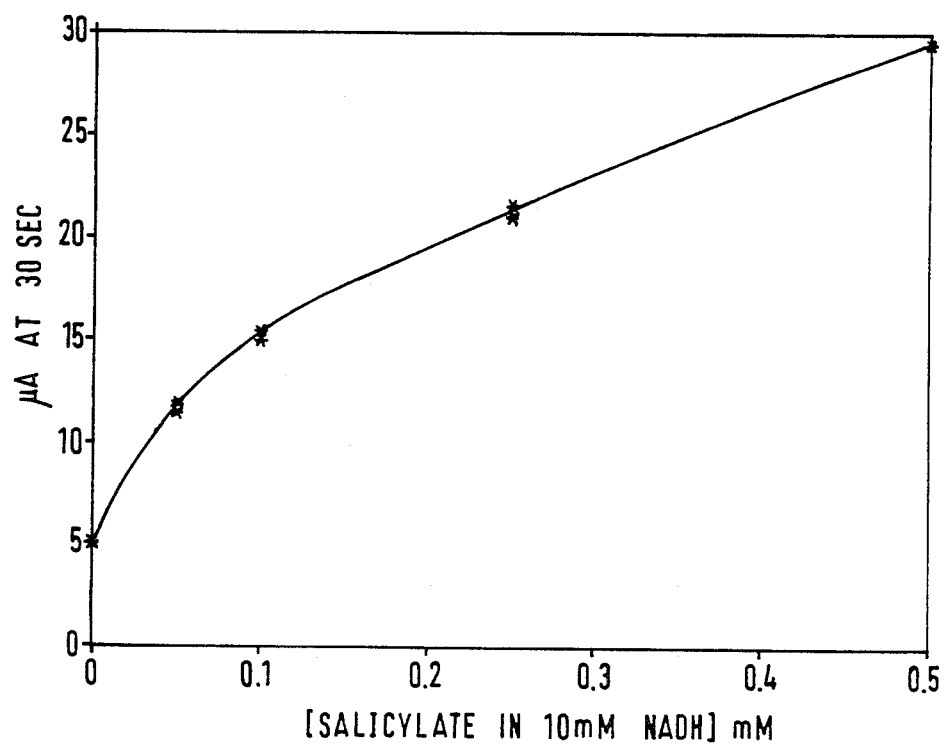
FIG. 7 shows a dry strip electrode response to salicylate.

Fixed potential studies were carried out at room temperature as described in Example 2 with the modification that the potential was poised immediately after the sample was applied. The calibration curve for salicylate is shown in FIG. 7.

We claim:

1. A method for the assay of salicylate ion, which comprises the steps of:
   (a) providing a sensor comprising an electrode having at its working surface a layer comprising salicylate hydroxylase and NAD(P)H;
   (b) contacting a liquid sample with said sensor, said salicylate hydroxylase catalyzing conversion to catechol of salicylate ion present in said sample;
   (c) measuring the concentration of said catechol in said contacted sample by direct electrochemical measurement of said catechol; and
   (d) relating said measured catechol concentration to the concentration of salicylate in said sample.

2. A method as claimed in claim 1 wherein an electrode set at a suitable potential contacts the liquid sample for direct electrochemical measurement of the catechol.

3. A method as claimed in claim 1 wherein the enzyme is a salicylate hydroxylase isolated from a bacterium.

4. A method as claimed in claim 3 wherein the bacterium is a species of Pseudomonas.

5. A method as claimed in claim 3 in which the salicylate hydroxylase is purified by liquid chromatography.

6. A method as claimed in claim 5 in which the salicylate is hydroxylase purified on an anion column by fast protein ion exchange chromatography.

7. A method as claimed in any one of claims 1-6 in which the sample is whole blood, serum or plasma.

* * * * *

UNITED STATES PATENT AND TRADEMARK OFFICE
CERTIFICATE OF CORRECTION

PATENT NO.    : 4,777,132
DATED         : October 11, 1988
INVENTOR(S)   : Monika J. Green et al.

It is certified that error appears in the above-identified patent and that said Letters Patent is hereby corrected as shown below:

Column 6,
Line 63, replace "is hydroxylase" with -- hydroxylase is --.
Line 65, replace "1-6" with -- 2,3,4,6,7, --.

Signed and Sealed this

Twenty-sixth Day of August, 2003

JAMES E. ROGAN
*Director of the United States Patent and Trademark Office*